US010105496B2

(12) United States Patent
Aneas

(10) Patent No.: US 10,105,496 B2
(45) Date of Patent: Oct. 23, 2018

(54) AUTOMATIC INJECTOR

(71) Applicant: BIOCORP PRODUCTION, Issoire (FR)

(72) Inventor: Antoine Aneas, Menetrol (FR)

(73) Assignee: Biocorp Production, Issoire (FR)

(*) Notice: Subject to any disclaimer, the term of this patent is extended or adjusted under 35 U.S.C. 154(b) by 92 days.

(21) Appl. No.: 15/110,933

(22) PCT Filed: Jan. 19, 2015

(86) PCT No.: PCT/EP2015/050848
§ 371 (c)(1),
(2) Date: Jul. 11, 2016

(87) PCT Pub. No.: WO2015/107180
PCT Pub. Date: Jul. 23, 2015

(65) Prior Publication Data
US 2016/0331905 A1 Nov. 17, 2016

(30) Foreign Application Priority Data

Jan. 20, 2014 (FR) ..................................... 14 50417

(51) Int. Cl.
*A61M 5/315* (2006.01)
*A61M 5/20* (2006.01)
*A61M 5/32* (2006.01)

(52) U.S. Cl.
CPC .......... *A61M 5/31571* (2013.01); *A61M 5/20* (2013.01); *A61M 5/2033* (2013.01);
(Continued)

(58) Field of Classification Search
CPC ............ A61M 5/31571; A61M 5/2033; A61M 5/3234; A61M 2005/2026; A61M 2005/208
See application file for complete search history.

(56) References Cited

U.S. PATENT DOCUMENTS

2005/0222539 A1\* 10/2005 Gonzales ............ A61M 5/2033
604/207

FOREIGN PATENT DOCUMENTS

EP 0666084 A2 8/1995
EP 2438947 A1 4/2012
(Continued)

OTHER PUBLICATIONS

International Preliminary Report on Patentability issued in application No. PCT/EP2015/050848 dated Dec. 18, 2015.
(Continued)

*Primary Examiner* — Nathan R Price
*Assistant Examiner* — Melissa A Snyder
(74) *Attorney, Agent, or Firm* — Knobbe, Martens, Olson & Bear, LLP

(57) ABSTRACT

An automatic injector includes a cover extending along a longitudinal axis. A syringe for injecting a drug is arranged inside the cover, and includes a needle, a needle protector, a body, a plunger, and a rod for pushing the plunger into the syringe body, which is moved axially forwards by a resilient load force exerted by a first spring during an injection. The syringe also includes a tip for protecting the needle, which is axially movable about the needle and against a resilient load force exerted by a second spring between a forward position in which the tip surrounds the needle and a retracted position in which the needle is uncovered. A mechanism blocks the forward movement of the rod. The mechanism is deactivated as the tip is moved towards the retracted position and is reactivated during the injection when the tip is moved towards the forward position.

9 Claims, 9 Drawing Sheets

(52) U.S. Cl.
CPC ........ *A61M 5/3204* (2013.01); *A61M 5/3234* (2013.01); *A61M 2005/208* (2013.01); *A61M 2005/2026* (2013.01)

(56) References Cited

FOREIGN PATENT DOCUMENTS

| | | | |
|---|---|---|---|
| EP | | 2468329 A1 | 6/2012 |
| WO | WO 2010/035060 A1 | | 4/2010 |
| WO | WO 2015/107180 A1 | | 7/2015 |

OTHER PUBLICATIONS

International Search Report and Written Opinion issued in application No. PCT/EP2015/050848 dated Mar. 19, 2015.

\* cited by examiner

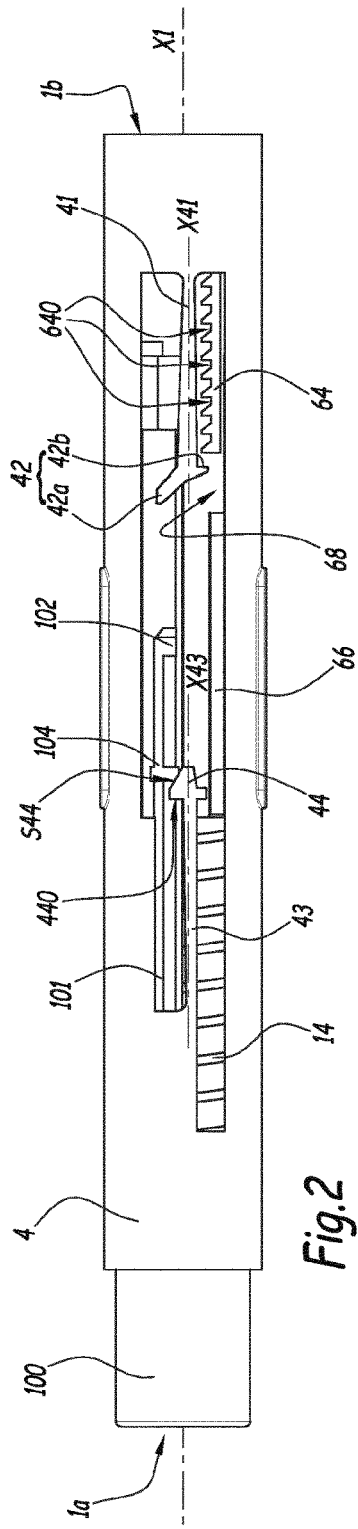
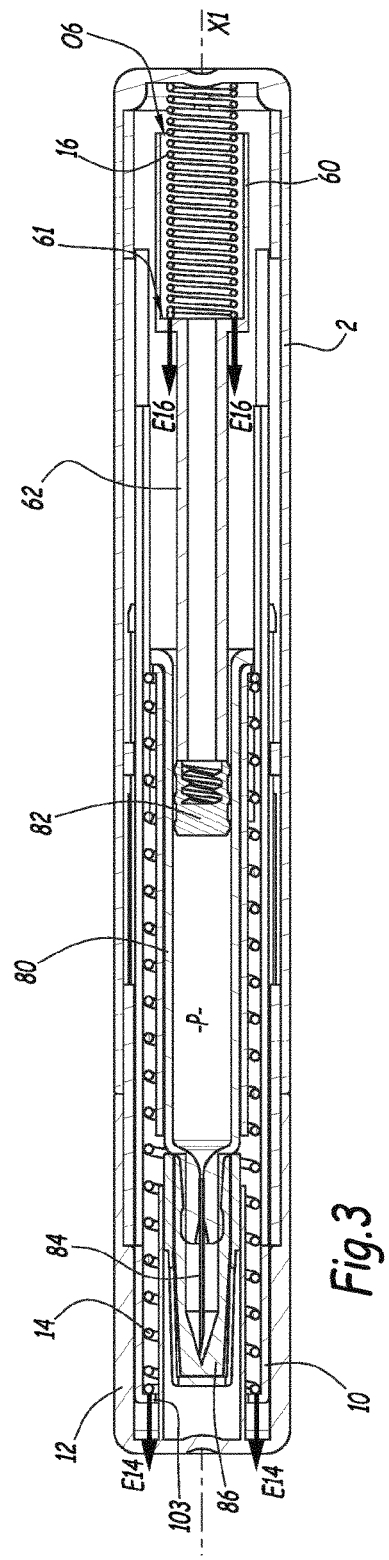
Fig.2
Fig.3

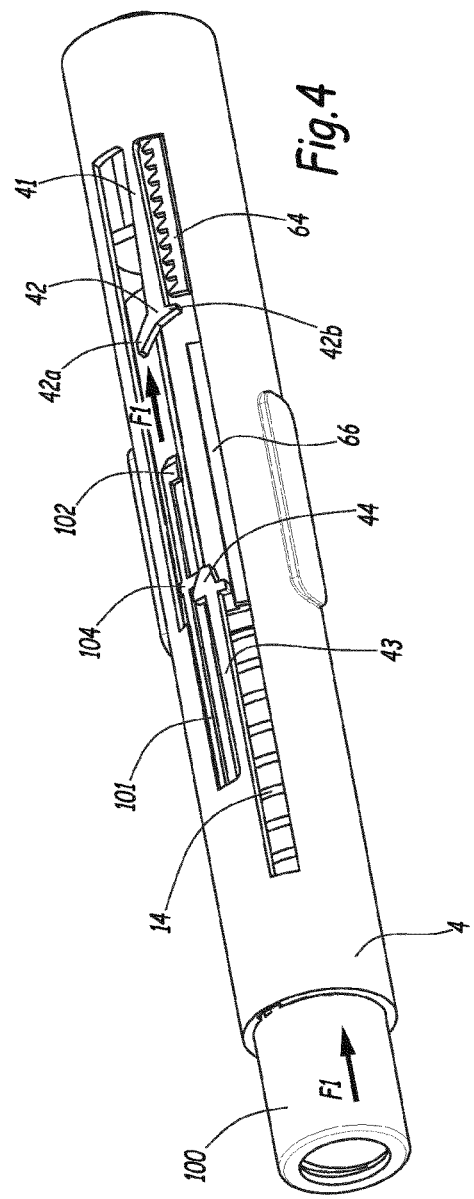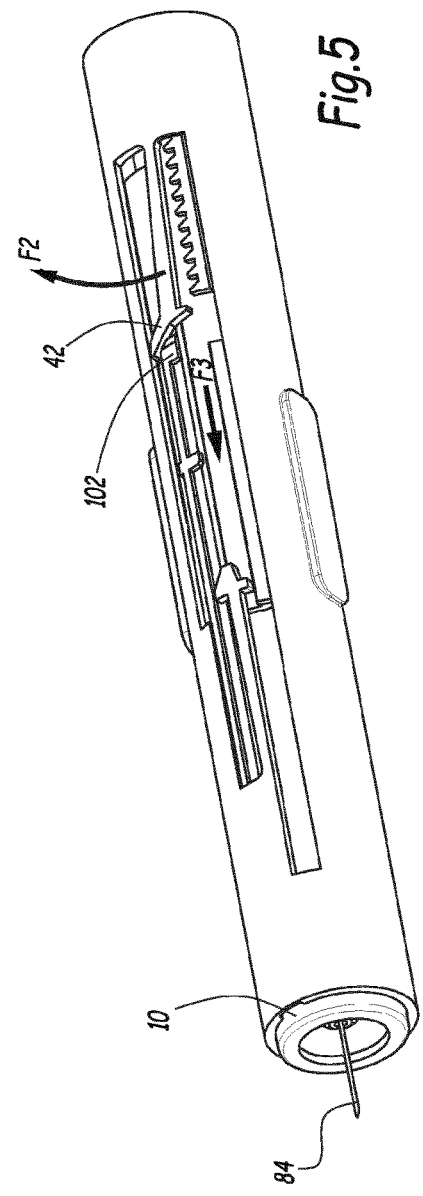

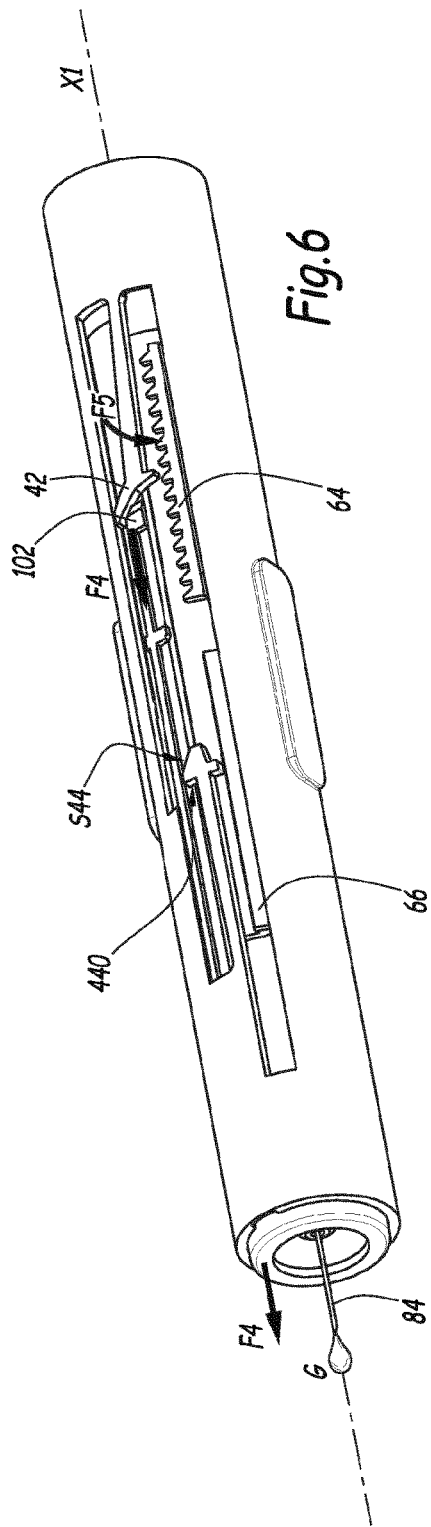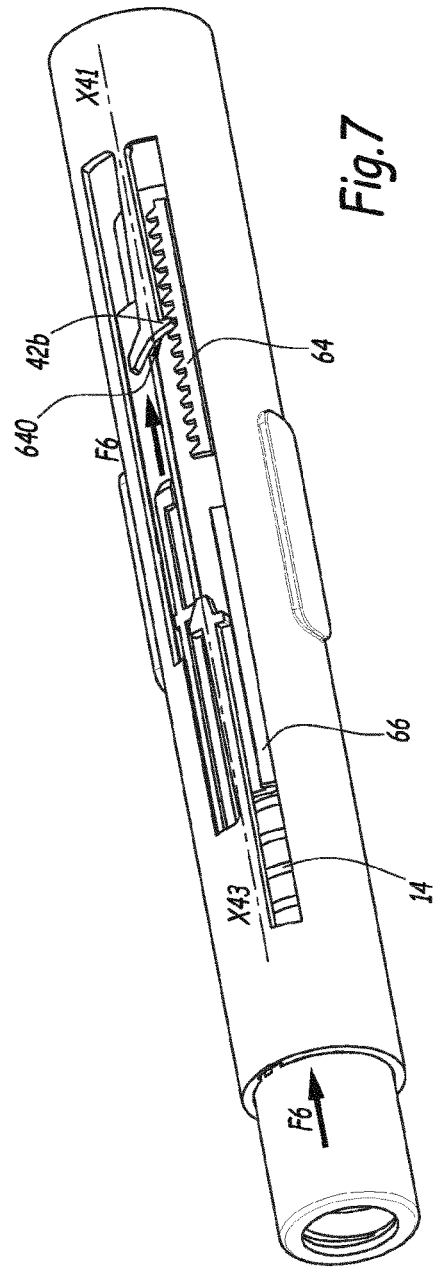

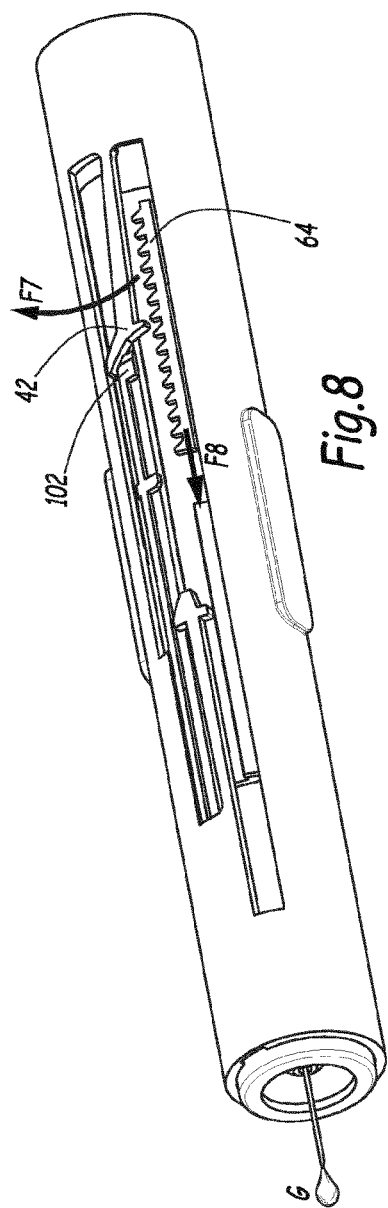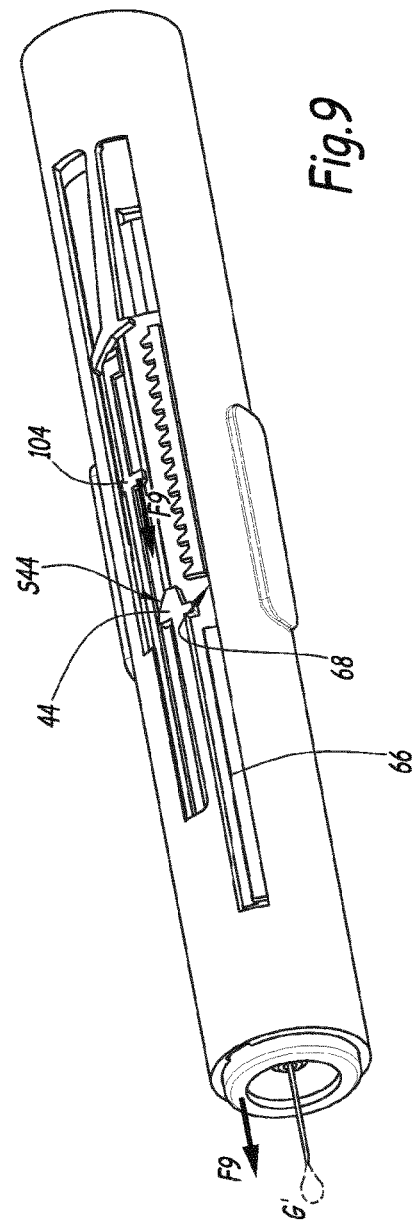

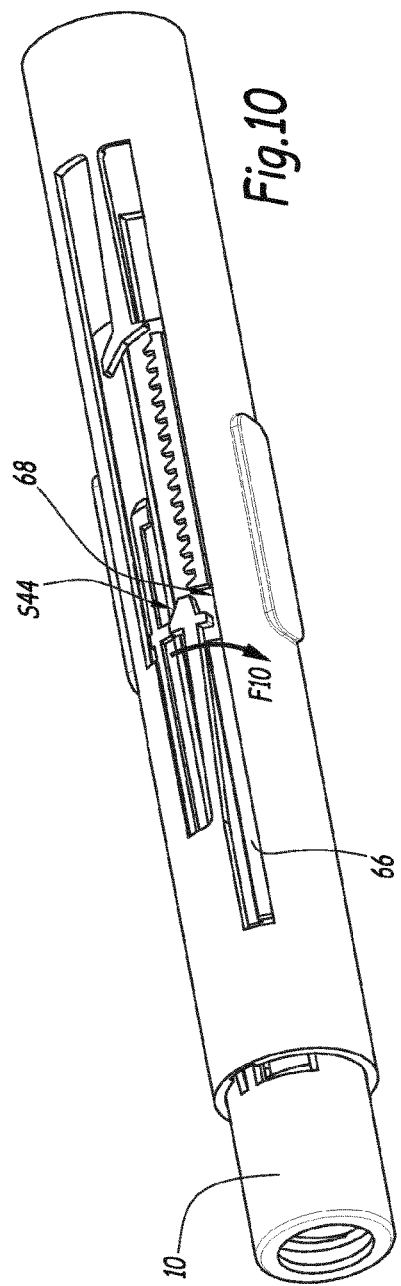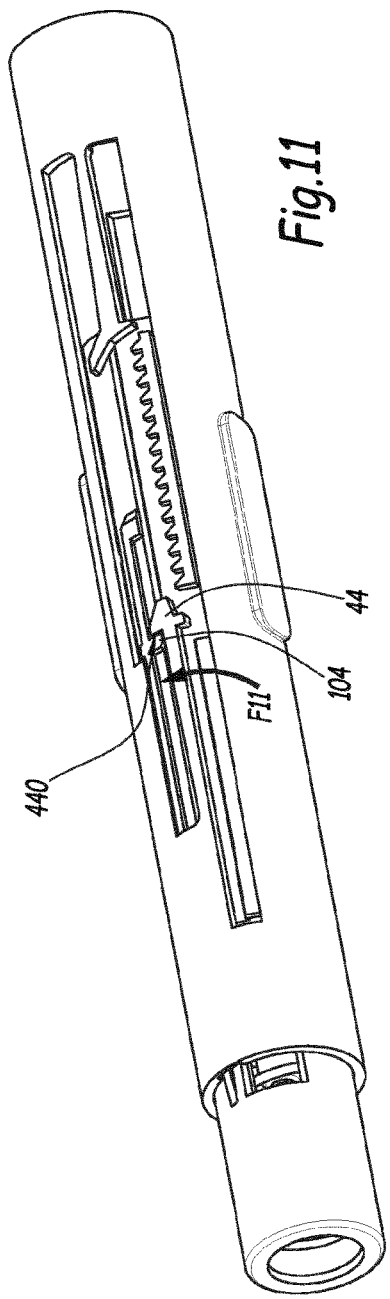

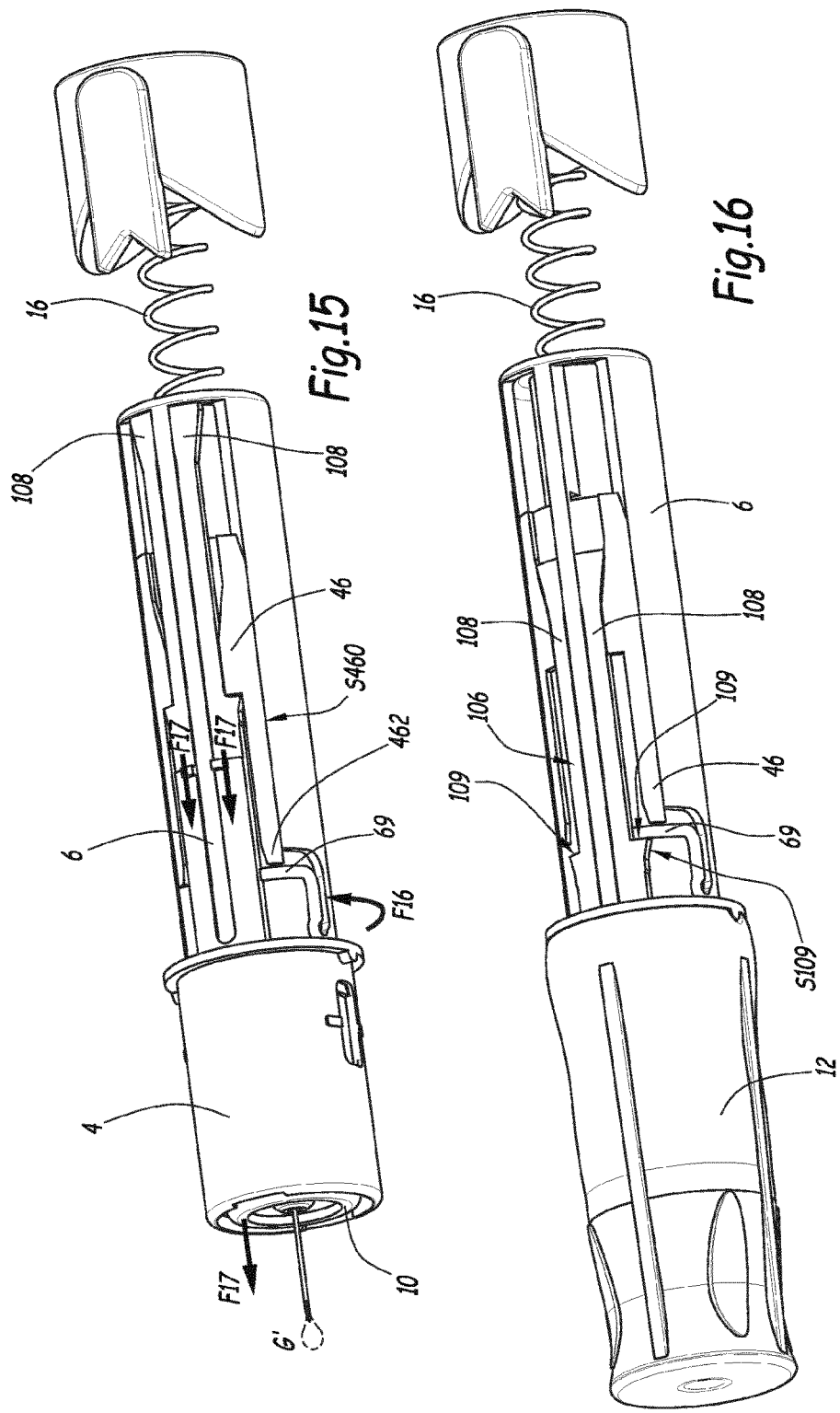

AUTOMATIC INJECTOR

This application is the U.S. National Phase under 35 U.S.C. § 371 of International Application No. PCT/EP2015/050848, filed Jan. 19, 2015, designating the U.S., and published in French as WO 2015/107180 A1 on Jul. 23, 2015, which claims priority to French Patent Application No. 1450417, filed Jan. 20, 2014, the entire contents of which are incorporated herein by reference.

BACKGROUND OF THE INVENTION

Field of the Invention

The present invention relates to an automatic injector, or auto-injector.

In the medical field, medicaments for emergency treatment are stored in glass syringes equipped with a glued needle, a piston and a needle protector. These syringes are generally inserted into the body of an auto-injector, to facilitate the administration of the medicament.

Auto-injectors are particularly well suited to urgent situations such as gas poisoning, a serious allergic reaction or heart attack. Indeed, in some cases, soldiers use auto-injectors in case of chemical attack to administer themselves a dose of atropine. Likewise, auto-injectors are often used to inject adrenaline into a patient's body suffering from a heart attack or an allergic reaction.

An auto-injector comprises a globally tubular housing, which contains the syringe housing the medicament. The injection of the medicament into the patient's body is obtained using a first spring that expands to push a piston in the syringe. In practice, the auto-injector is provided with a push rod for the piston, which is retained by blocking means.

Description of Related Art

FR-A-2,654,938 discloses an auto-injector in which these blocking means are formed by a retaining clip of the rod, comprising elastic fingers gripping the rod. The fingers of the clip may be separated from the rod by using a corner device, and the force transmitted to the fingers comes from a pushbutton positioned behind the auto-injector. The separation of the fingers of the clip makes it possible to release the gripping force of the clip on the rod, which frees the forward movement of the piston under the action of the resilient load of the first spring.

FR-A-2,733,155 and WO-A-94/11041 each disclose an auto-injector in which the means for blocking the forward movement of the piston comprise an elastic retaining ring, which is positioned around the rod and which has an inner diameter smaller than the maximum diameter of the rod. These blocking means further comprise an outer sleeve, which is movable in a direction parallel to the movement axes of the rod, between a locked position, where it is positioned radially around the elastic ring and where it prevents the radial expansion of the elastic ring under the resilient load force of the first spring, and a withdrawn position, where it does not prevent the elastic deformation of the ring. In this way, the rod cannot pass through the ring as long as the sleeve has not been withdrawn and the movement of the piston inside the syringe is blocked. In FR-A-2,733,155, the sleeve is placed under a resilient load by a spring in its locked position and can be withdrawn by the user to free the rod, in particular using an outer indentation. In WO-A-94/11041, the guide sleeve is placed under a resilient load by a spring toward its withdrawn position and is kept in position by a slug. This slug can be withdrawn by unsticking a tongue, or pin, so as to free the expansion of the spring acting on the sleeve.

EP-A-0,666,084 also discloses an auto-injector, in which the means for blocking the forward movement of the piston comprise a latch, which is engaged in a notch of the rod. This latch can be freed from its notch by pressing on a transverse button of the pen. It thus frees the forward movement of the rod. Furthermore, this auto-injector includes a pushbutton, or protective end-piece of the needle, which is withdrawn in contact with the epidermis against the resilient load action of a second spring. Thus, when the auto-injector is removed from the patient's body, the end-piece covers the needle under the action of the resilient load from the second spring. Nevertheless, this covering movement does not cause the movement of the piston to stop, i.e., the injection is not stopped.

The problem with the aforementioned auto-injector is that, when the push rod of the piston is freed, the injection is done without stopping. Yet soldiers suffering from gas poisoning or patients in a state of stress may shake during the injection and accidentally withdraw the injector from the targeted part of their body, such that they do not manage to inject all of the medicament. Thus, if for any reason the user withdraws the auto-injector from his body, the injection of the active ingredient continues in the open air. The injection is therefore incomplete and a certain amount of medicament is lost. This problem is resolved in EP-A-2,438,947 and EP-A-2,468,329.

In EP-A-2,438,947, the syringe is kept in a moving support inside the cap. The auto-injector comprises a rod able to successively push the syringe and the piston of the syringe under the resilient force of a spring and a protective end-piece of the needle, which is axially movable against elastic force generated by a spring.

When the auto-injector is pressed against a patient's epidermis, the protective end-piece is pushed back into the distal position. By maintaining or accentuating the pressure of the auto-injector in the epidermis, the syringe is moved in the proximal direction, such that the hollow needle penetrates inside the patient's epidermis. In a second step, the rod pushes the piston in the proximal direction, which makes it possible to discharge medicament from the syringe.

In EP-A-2,468,329, an unlocking sleeve is positioned around the outer cap and an inner tube, outwardly threaded, is arranged in a complementary tapped outer tube. The outer tube is subject to an elastic torque generated by a torsionally loaded spring. The rotation of the tube drives the forward movement of the inner tube and the translational movement of the piston inside the syringe. A wheel is mounted at the end of the outer tube. This wheel is equipped with outer teeth that cooperate with inner elastic lugs of the cap to prevent rotation of the outer tube under the yield moment of the spring. The unlocking sleeve includes an axial rim that opposes the tilting of the lugs toward the outside. When the auto-injector is pressed against a patient's epidermis, the unlocking sleeve moves axially forward and frees the lugs, such that the lugs can tilt radially outward and free the rotational movement of the wheel, i.e., of the outer sleeve, under the yield moment generated by the spring. The tube then advances in the forward direction, which results in pushing the syringe toward the front such that the hollow needle penetrates the patient's epidermis on the one hand, and the inner piston toward the inside of the syringe body such that medicament is discharged through the hollow needle into the patient's body on the other hand.

In EP-A-2,438,947 and EP-A-2,460,329, the injection step is completely automated by moving the syringe body to cause the needle to penetrate the epidermis. This automatic operation may surprise an uninformed user, since it is not conventional and may therefore lead to a poorly performed injection.

SUMMARY OF THE INVENTION

The invention more particularly aims to resolve these drawbacks by proposing an automatic injector with which the injection step remains manual and with which the injection of the active ingredient is stopped when the injector is withdrawn during the injection and with which the injection may resume if the user once again presses the injector on his body.

To that end, the invention relates to an automatic injector that comprises a cap, extending along a longitudinal axis, a syringe for injecting a medicament, which is positioned inside the cap and which includes a needle, a needle protector, a body and a piston, a rod for pushing the piston inside the syringe body, which is moved axially forward by a resilient load force exerted by a first spring, during an injection, a protective end-piece of the needle, which is axially movable around the needle and against a resilient load force exerted by a second spring, between an advanced position where it surrounds the needle and a withdrawn position, where the needle is exposed, and means for blocking the forward movement of the rod. The blocking means are configured to be deactivated when the end-piece is moved toward its withdrawn position or reaches that position, and to be reactivated during injection when the end-piece is moved toward its forward position or arrives in that position. The means for blocking the forward movement of the rod may comprise a first locking lever for the movement of the rod, which is provided to block the forward movement of a rack arranged on the push rod. The end-piece then comprises a cam freeing the blocking action of first lever on the rack, said cam driving the tilting of the first lever toward a free configuration of the rack when the end-piece arrives in the withdrawn position. Alternatively, the means for blocking the forward movement of the rod comprised two elastic fins, which belong to the end-piece and which are positioned on either side of the push rod, and two stops blocking the elastic fins in a position where the elastic fins keep the rod in a vise between them.

Owing to the invention, if for any reason the user withdraws the injector from his skin, i.e., partially or completely releases the pressure of the injector in contact with the skin, the protective end-piece of the needle returns to its withdrawn position and the means for blocking the forward movement of the piston inside the body of the syringe are reactivated. Thus, the injection of the medicament is stopped and there is no loss of medicament when the user withdraws the injector from his skin before the end of the injection. Furthermore, the user may end his injection by again applying the injector on a part of his body, since this again causes the end-piece to move toward its withdrawn position and causes the deactivation of the means blocking the forward movement of the rod. Lastly, the injection step remains manual so that the auto-injector is easily usable by everyone.

DETAILED DESCRIPTION

According to advantageous but optional aspects of the invention, an automatic injector may incorporate one or more of the following features, in any technically allowable combination:

The first lever is elastically deformable and is deformed at the beginning of injection in contact with the cam, to tilt off the passage trajectory of the rack.

The first lever is configured to resume its initial shape by elastic return if the end-piece returns toward its forward position during injection. This elastic return causes a part of the lever to be housed in an indentation of the rack, thus preventing the forward movement of the push rod.

The fins each comprise a bearing surface on a stop, which is inclined relative to a longitudinal axis of the rod parallel to the longitudinal axis and is complementary to a contact surface of the stop.

The automatic injector further comprises means for locking the end-piece in a forward end of injection position, which opposes the withdrawal of the end-piece after injection.

The means for locking the end-piece comprise an elastic finger belonging to the rod, which pivots at the end of injection by elastic return, to block the withdrawal of the fins of the end-piece.

The locking means comprise a second lever blocking the movement of the end-piece, which is provided to cooperate with a bolt worn by the end-piece, this second lever opposing the withdrawal of the bolt of the end-piece when the end-piece is in the end of injection position.

The second lever is elastically deformable and in that the rod comprises an anvil maintaining the second lever during the injection, which prevents the second lever from deforming in contact with the bolt as long as the injection is not complete.

The anvil is arranged on the rod to stop maintaining the second lever at the end of injection, the second lever then deforming in contact with the bolt to free the movement of the end-piece toward its end of injection position and regaining its initial shape by elastic return in a position where it opposes the withdrawal of the bolt of the end-piece.

BRIEF DESCRIPTION OF THE DRAWINGS

The invention and other advantages thereof will appear more clearly in light of the following description of two embodiments of an automatic injector according to the invention, done according to its principle and in reference to the drawings, in which:

FIG. 2 is a side view of the automatic injector of FIG. 1 where the injector is shown in the assembled position and an outer cap of the injector is omitted, FIG. 3 is a longitudinal sectional view of the automatic injector of FIGS. 1 and 2, FIGS. 4 to 11 respectively show perspective views of the automatic injector of FIGS. 1 to 3, in which the outer cap of the injector is omitted and which show successive positions of the injector during the injection, and FIGS. 12 to 16 are perspective views, on different scales, of an automatic injector according to a second embodiment of the invention, which show successive positions of the injector during the injection.

FIG. 1 shows an automatic injector or auto-injector 1. In FIG. 1, all of the components of the auto-injector 1 are not shown on the same line for clarity of the drawing. However, all of the components of the injector 1 are in practice aligned along a same longitudinal axis X1. Indeed, the auto-injector 1 looks like the pen, i.e., has a globally cylindrical shape centered on the axis X1.

Figure 1:
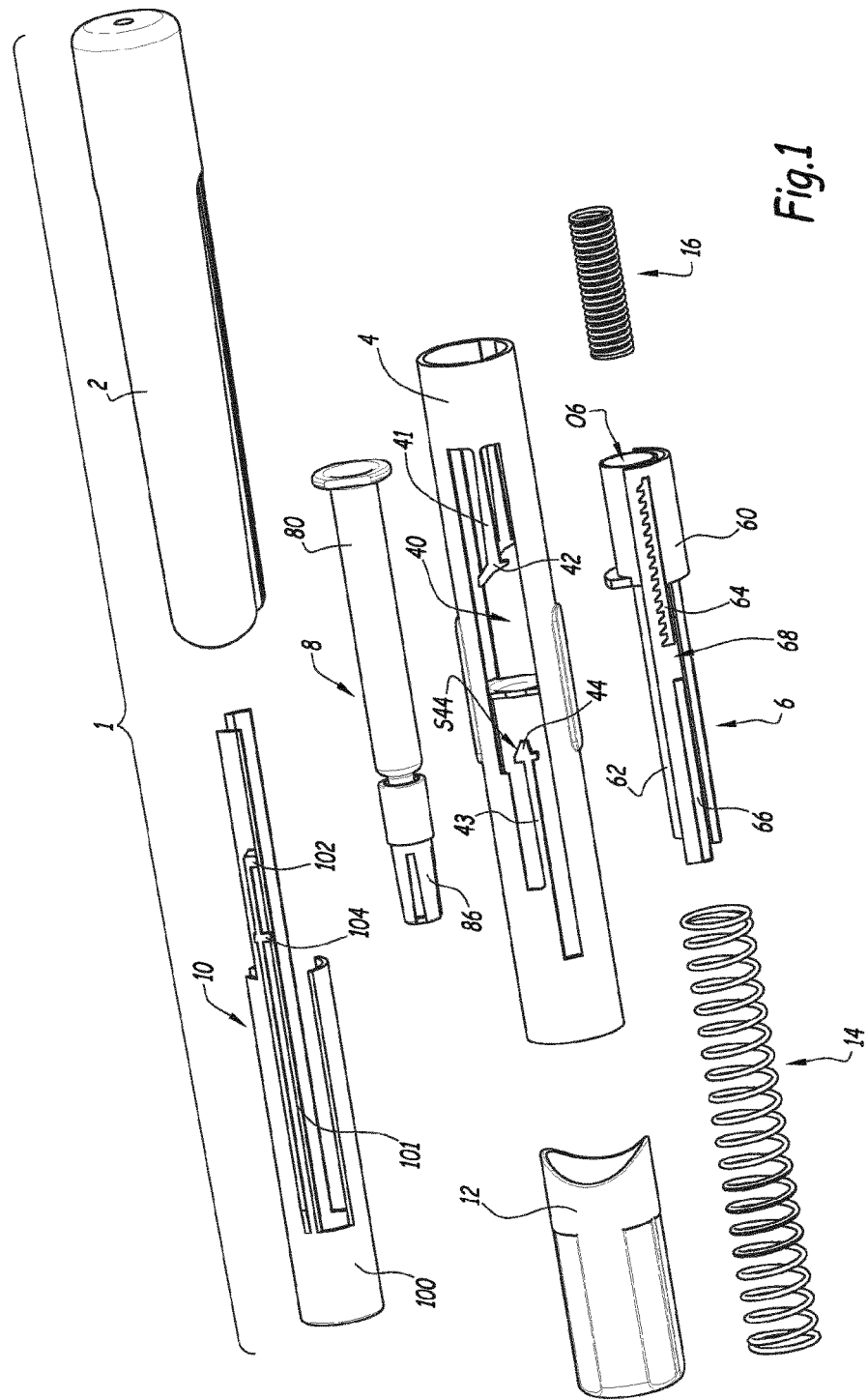
FIG. 1 is an exploded perspective view of an automatic injector according to the invention.

The injector 1 comprises an outer shell or cap 2 that has a globally tubular geometry, centered on the longitudinal axis X1 in the mounted configuration of the injector 1.

As shown in FIG. 2, the injector 1 comprises a first longitudinal end 1a, which is provided to be turned toward the epidermis during an injection, and a second longitudinal end 1b, which is opposite the end 1a along the axis X1.

In FIGS. 2 and 4 to 11, the cap 2 is omitted for better viewing of the inner components of the injector 1.

A tubular enclosure 4 is positioned coaxially inside the cap 2 and is immobile relative to the latter.

In the rest of the description, the "forward" direction designates a direction going from the end 1b toward the end 1a, and the opposite for the "rear" direction. Likewise, a longitudinal direction designates a direction parallel to the longitudinal axis X1.

An end-piece, or pusher, 10 with a globally tubular geometry is positioned coaxially to the inside of the enclosure 4. The end-piece 10 comprises a front part 100 that protrudes forward relative to the enclosure 4 when the injector 1 is idle. The end-piece 10 is subject to the resilient load action of a spiral spring 14, which is arranged inside the tubular enclosure 4, in contact with the end-piece 10.

The part 100 includes a front end 103 that is radially curved inward relative to the axis X1. The end 103 forms an inner radial shoulder on which the spiral spring 14 bears, while exerting a resilient load force E14 oriented forward. The end-piece 10 also includes a tab 101 that extends longitudinally from the part 100 toward the rear. This tab 101 bears a bolt 104 and a cam 102 that is positioned behind the bolt 104.

The enclosure 4 also contains a syringe 8 for administering or injecting a medicament P. In practice, the medicament or active ingredient P may be an atropine solution, which is an antidote for gas poisoning, or an adrenaline solution, used in case of heart attacks or serious allergic reactions. The syringe 8 includes a glass body 80, a hollow needle 84 and a piston 82 that is mounted axially inside the body 80. The piston 82 is sometimes called "piston seal" in the medical field, since it involves an elastomer sealing gasket. The needle 84 is glued to the body 80 and is protected by a cover or needle protector 86. Furthermore, the part 100 of the end-piece 10 is provided to protect the needle 84 when the cover 86 is removed, in order to avoid accidentally being stuck with said needle.

A rod 6 for pushing the piston 82 inside the syringe body 80 is also positioned inside the tubular enclosure 4. This rod 6 is made from plastic and is arranged axially with the syringe 8. It is also subject to the resilient load action of a spiral spring 16.

Lastly, a cap 12 makes it possible to plug the automatic injector 1 when the latter is not in use. The cap 12 is secured axially or in translation with the needle protector 86. Indeed, the cap 12 comprises tabs that surround the needle protector 86 and are attached, or "clipped", in the needle protector 86. Thus, the withdrawal of the cap 12 jointly causes the withdrawal of the needle protector 86 from the syringe 8.

The tubular enclosure 4 defines a cutout 40, the contour of which is globally rectangular. An injection lever 41 extends from a rear lateral edge of the cutout 40 in the forward direction. Reference X41 designates a longitudinal axis of the lever 41. The lever 41 includes a front end 42, formed by two branches 42a and 42b that extend transversely to the longitudinal axis X41 of the lever 41.

Furthermore, a guard lever 43 extends toward the rear from a front edge of the cutout 40, i.e., from an edge opposite the attachment edge of the lever 41. Reference X43 designates a longitudinal axis of the lever 43. This guard lever 43 includes a rear end 44, having a contact surface S44 with the bolt 104 and a shoulder 440 for blocking the bolt 104. The surface S44 is an inclined surface, which converges rearward toward the axis X43. The enclosure 4 is made from plastic and the levers 41 and 43 are elastically deformable.

The rod 6 for pushing the piston 82 includes, at the rear, a tubular body 60 including an opening O6 for the passage of the spring 16 and a hollow tail 62 that extends from the body 60 in the forward direction and that is provided to push the piston 82 during injection. To that end, the tail 62 is partially inserted into the syringe body 80, in contact with the piston 82. The rod 6 comprises an inner radial shoulder 61, which is positioned at the junction between the body 60 and the tail 62 and forms a bearing surface of the spiral spring 16. The spiral spring 16 exerts a resilient load force E16 oriented forward on the shoulder 61.

The rod 6 bears a longitudinal rack 64 provided with several indentations 640. This rack 64 is positioned behind the tail 62, in particular at the same axial level as the body 60. The rod 6 also bears an anvil 66, which is positioned forward relative to the rack 64. The anvil 66 and the rack 64 define a hollow space between them, or housing 68.

The end-piece 10 is axially movable, around the needle 84 and coaxially inside the enclosure 4, between a forward position, where it protects, or surrounds, the needle 84, and a withdrawn position, where the needle 84 is exposed. The withdrawn position is for example shown in FIG. 5. In the example, the forward position is an armed position of the auto-injector 1, which is shown in FIG. 4. In this position, the auto-injector 1 is ready to be used, i.e., the cover 86 is withdrawn.

The movement of the end-piece from its forward position to its withdrawn position is done against the resilient load force E14 from the spiral spring 14, i.e., that the spring 14 comprises during the withdrawal of the end-piece 10.

In the forward position of the end-piece 10, the injection lever 41 blocks the forward movement of the rod 6. Indeed, the branch 42b of the end 42 belonging to the lever 41 blocks the forward movement of the rack 64 equipping the rod 6. More specifically, the branch 42b of the end 42 is positioned on the forward trajectory of the rack 64. In other words, the branch 42b forms an obstacle to the passage of the rack 64.

The lever 41 and the rack 64 therefore together form means for blocking the forward movement of the rod 6. These means for blocking the forward movement of the rod 6 are initially activated when the end-piece 10 is in the forward position.

In the forward position of the end-piece 10, the bolt 104 of the tab 101 abuts against the surface S44 of the end 44 of the lever 43. More specifically, the bolt 104 bears against the surface S44 in the forward direction. The end 44 of the lever 43 therefore blocks the forward movement of the bolt 104 and the surface S44 is a blocking surface for the forward movement of the end-piece 10.

More specifically, the end 44 of the lever 43 is inserted, in a direction orthoradial to the axis X1, between the bolt 104 and the anvil 66 of the rod 6. Indeed, the end 44, the bolt 104 and the anvil 106 are positioned at the same axial level and the end 44 is jammed, considering a direction orthoradial to the axis X1, between the bolt 104 and the anvil 66. The anvil 66 thus prevents the lever 43 from deforming elastically under the bearing action of the bolt 104, this action being oriented in the forward direction. The lever 43 therefore retains its initial shape and prevents the bolt 104 from moving forward, under the action of the spring 14.

To perform an injection, the user withdraws the cap 12 from the injector 1 and brings the needle protector 86 with the cap 12, since they are axially secured to one another. The injector is then ready to be used and the end-piece 10 is in its forward position, as shown in FIG. 4.

Next, the user presses the injector 1 on part of his body, such as his thigh. To do this, the user brings the end 1a of the injector 1 against his thigh and presses, for example, on the end 1b toward his thigh. This causes a withdrawal of the end-piece 10 in contact with the skin, this withdrawal being represented by arrow F1 in FIG. 4. The end-piece 10 therefore exposes the needle 84 in its movement and the needle 84 penetrates the epidermis in parallel with the withdrawal F1 of the end-piece 10. The cam 102 of the tab 101 withdraws with the rest of the end-piece 10 and then comes into contact with the end 42 of the injection lever 41, i.e., the end-piece 10 comes into the withdrawn position.

As shown in FIG. 5, when the cam 102 comes into contact with the end 42 of the lever 41, the lever 41 deforms elastically under the thrust action of the cam 102 in the rear direction. This deformation of the lever 41 is a flexion F2 that is oriented opposite the rack 64, in a direction globally orthoradial to the axis X1. The flexion F2 causes the branch 42b of the end 42 to free itself from the forward trajectory of the rack 64, i.e., the lever 41 tilts toward a free configuration of the rack 64, which frees the forward movement of the rod 6 under the resilient load force E16 from the spring 16. The rod can then move forward, as shown by arrow F3 in FIG. 5. Thus, the movement of the end-piece 10 in its withdrawn position drives the deactivation of the means blocking the forward movement of the rod 6.

The forward movement F3 of the rod 6 drives the beginning of the injection, i.e., the piston 82 is pushed inside the syringe body 80 by the tail 62 and forces the active ingredient P contained in the body 80 to leave through the hollow needle 84. The injection of the active ingredient P from the syringe 8 is shown in FIG. 6 by the appearance of a drop G at the end of the needle 84.

Furthermore, if the user partially releases the pressure of the injector 1 on his thigh, the end-piece 10 leaves its withdrawn position, i.e., it returns toward its forward position owing to the force E14, by relaxation, or elastic return, of the spring 14. Thus, the cam 102 ceases to act on the injection lever 41 and the branch 42b returns to be elastically engaged with the rack 64. The movement, during injection, of the end-piece 10 toward its forward position therefore drives the reactivation of the means blocking the forward movement of the rod 6. In this embodiment, it is not necessary for the end-piece 10 to reach the forward position to deactivate the means blocking the forward movement of the rod 6. Indeed, once the end-piece 10 leaves its withdrawn position, i.e., the user releases the pressure of the auto-injector 1 on his thigh, the means for blocking the forward movement of the rod 6 are reactivated.

If the user completely removes the auto-injector 1 from his thigh, the end-piece 10 comes into its withdrawn position and is blocked in its forward movement. Indeed, as explained above, the movement of the bolt 104 in the forward direction is blocked by the end 44 of the lever 43, in cooperation with the anvil 66.

A partial or total release of the pressure of the auto-injector 1 on the user's body drives a return of the end-piece 10 toward its forward position, as shown by arrows F4 in FIG. 6. Following this movement, the lever 41 regains its initial shape by elastic return toward the rack 64. The elastic return movement of the lever 41 is shown in FIG. 6 by arrow F5 and means that the branch 42b of the end 42 becomes housed in an indentation 640 of the rack 64. The movement of the rack 64 is then blocked by the lever 41. The rod 6 is then immobilized and the injection of the medicament is temporarily stopped.

Thus, if for any reason the user withdraws the injector 1 from his thigh, the injection is stopped and no medicament is lost. This is particularly advantageous since, in urgent situations such as a heart attack, an allergic reaction or a chemical gas attack, the user is generally in a state of stress and may shake, and therefore accidentally remove the auto-injector from his thigh.

The user may subsequently resume the injection by pressing on his thigh again to cause the end-piece 10 to withdraw. As previously described, a new withdrawal of the end-piece 10, shown by arrow F6 in FIG. 7, causes a withdrawal over the same travel of the cam 102, which comes back into contact with the end 42 of the injection lever 41. The contact action of the cam 102 in contact with the end 42 again causes tilting F7 of the lever 41, outside the indentation 640 of the rack 64. The rack 64 is then freed from the retaining action of the lever 41 and the forward movement of the rod 6 continues, as shown by arrow F8 in FIG. 8. This means that the injection continues, as shown by the drop G in FIG. 8.

When the injection is complete, generally after a duration of 4 to 8 seconds, the user withdraws the auto-injector 1 from his thigh and the end-piece 10 advances under the effect of the force E14, as shown by arrows F9 in FIG. 9. In FIG. 9, the end of the injection phase is shown by a drop G', the outline of which is diagrammatically drawn in broken lines.

At the end of the injection, the end 44 of the lever 43 is no longer positioned at the same axial level as the handle 66, since the anvil 66 is moved forward following the forward movement of the rod 6 and has protruded past the end 44. The anvil 66 is then in front of the end 44 of the lever 43. More specifically, the end 44 is at the same axial level as the housing 68 inserted between the anvil 66 and the rack 64.

During the forward movement of the end-piece 10, the bolt 104 comes into contact with the surface S44 of the end 44 and the thrust force from the bolt 102 in the forward direction, on the surface S44, drives tilting F10 of the lever 43 such that the end 44 becomes temporarily housed in the housing 68 of the rod 6. Indeed, the anvil 66 no longer prevents the elastic deformation of the guard lever 43. The bolt 104 of the end-piece 10 therefore passes in front of the end 44 of the lever 43. The end-piece 10 is then in a forward end of injection position shown in FIG. 11, which is a position even further forward relative to the forward position.

Once the bolt 104 has protruded past the end 44, i.e., when the end-piece 10 reaches the end of injection position, the lever 43 regains its initial shape by elastic return F11. The shoulder 440 of the end 44 then opposes the withdrawal of the end-piece 10. In other words, the shoulder 440 forms a stop blocking the withdrawal movement of the bolt 104. The lever 43 and the bolt 104 therefore together form means for locking the end-piece 10 in a forward end of injection position, which oppose the withdrawal of the end-piece after the injection. This constitutes a safety for the user, since the needle 84 can no longer be exposed after the injector has been used. There is therefore no risk of being accidentally stuck by the needle 84, and the end-piece 10 is kept in the end of injection position.

FIGS. 12 to 16 show a second embodiment of the automatic injector 1. Below, only the differences with respect to the first embodiment are described in the interest of concision. Furthermore, the elements of the injector 1 that are identical or that work similarly to those of the injector of the first embodiment retain their numerical reference, while the additional elements or those which work differently bear other numerical references.

In this second embodiment, the end-piece 10 also includes a front part 100 that protrudes past the tubular enclosure 4 in the forward direction. Two fins 106 extend from the body 100 toward the rear. These fins 106 are elastically deformable and each include a rear end 108. Furthermore, the auto-injector 1 is symmetrical relative to a median plane containing the longitudinal axis X1. Thus, two other fins are positioned on the side opposite the viewing angle of FIGS. 12 to 16. In the rest of the description, only the elements positioned on the visible side are described, since the corresponding symmetrical elements are identical.

A tail 62 belonging to a push rod 6 for pushing the piston inside the syringe body is engaged in a vise with the two ends 108 of the fins 106. More specifically, the tail 62 has a width, measured in a direction orthoradial to the axis X1, that is greater than or equal to the separation between the fins 106, measured along the same direction.

The ends 108 of the fins 106 each include a bearing surface S108A against the tail 62 of the rod 6 and an inclined surface S108B, which is opposite bearing surface S108A on the tail 62. More specifically, the surfaces S108B diverge, relative to a longitudinal axis X62 of the tail 62, toward the rear. The surfaces S108A and S108B are identified in FIG. 14, where only the outer radial outline of the surfaces S108A is visible, since they bear against the tail 62. These surfaces S108A are parallel to one another and to the axis X1.

The surfaces S108B are complementary to two surfaces S46 belonging to two seats 46. In other words, the surfaces S46 diverge toward the rear relative to the longitudinal axis X62 of the tail 62, with the same incline as that of the surfaces S108B. The seats 46 belong to the enclosure 4 and are positioned at the same axial level. The fins 106 are positioned between these two seats 46 and on either side of the tail 62, relative to a direction orthoradial to the axis X1.

The rod 6 is continuously subject to a resilient load force of a spring 16, which tends to push the rod 6 forward. The thrust force of the rod 6, which is similar to the force E16 of the first embodiment, tends to separate the fins 106 from one another by elastic deformation, to allow the tail 62 to pass.

Figure 13:
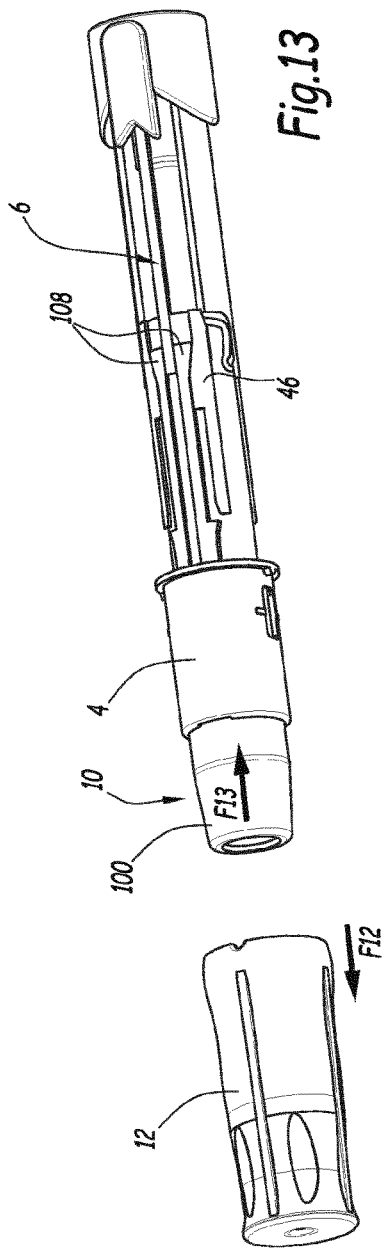

As in the first embodiment, the end-piece 10 is axially mobile against the resilient load action of the spring (not shown) and comparable to the spring 14, between a forward position, shown in FIG. 13, and a withdrawn position, shown in FIG. 15.

Figure 12:
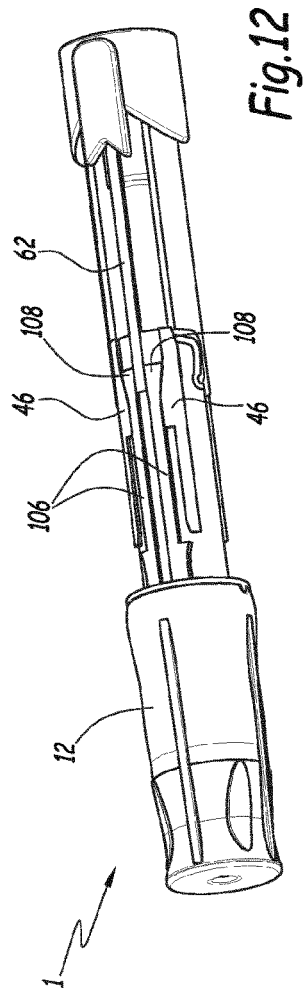

When idle, i.e., in the forward position of the end-piece 10, which is shown in FIGS. 12 and 13, the surfaces S108B of the ends 108 of the fins 106 bear against the surfaces S46 of the seats 46. Thus, the seats 46 prevent the fins 106 from deforming elastically to allow the tail 62 of the rod 6 to pass. The seats 46 therefore form, with the fins 106, means for blocking the forward movement of the rod 6. These means for blocking the forward movement of the rod 6 are initially activated when the end-piece 10 is in the forward position.

Furthermore, a finger 69 borne by the push rod 6 is in contact with a surface S460 of a seat 46, on the side opposite the fins 106. This finger 69 is elastic or elastically deformable. When idle and more generally as long as the injection is not complete, the finger 69 is crushed, or compressed against the surface S460 of the stops 46. Furthermore, the surface S460 is opposite the surface S46 of the stops 46.

The fins 106 further each include, in front relative to the ends 108, a shoulder 109 that widens the fins 106 and is turned toward the rear. S109 designates a lateral surface of the fins 106, this surface being positioned in the extension of the surface S108 in the forward direction, after having passed the shoulder 109.

Figure 14:
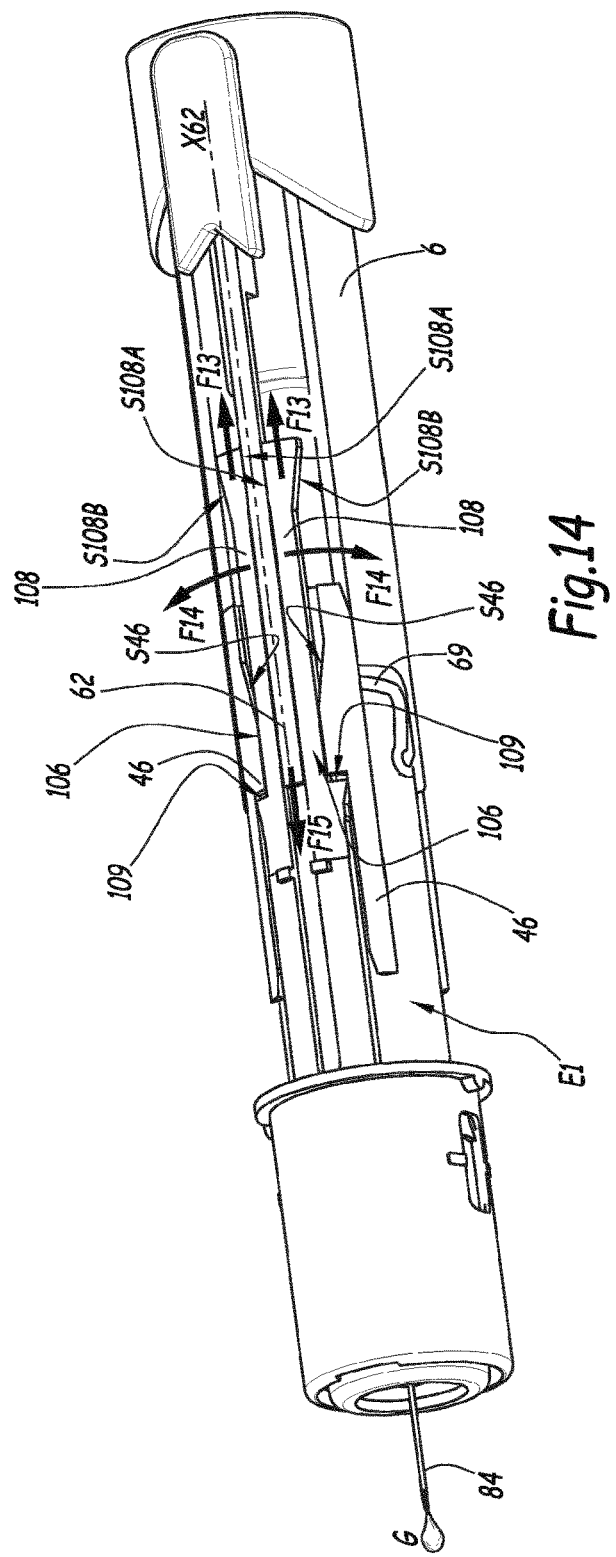

To perform an injection, the user moves the cap 12 as shown by arrow F12 in FIG. 13 and brings, as in the first embodiment, the needle protector 86 with the cap 12, since the latter are axially secured to one another. The user then presses the injector 1 on part of his body, for example his thigh. The contact action of the injector 1 on the user's thigh tends to cause the end-piece 10 to withdraw, as shown by arrow F13 in FIG. 13. The ends 108 of the fins 106 then unstick from the seats 46, as illustrated in FIG. 14.

In this position, the ends 108 of the fins 106 are no longer maintained by the seats 46 firmly bearing against the tail 62, such that the fins 106 can deform elastically. The resilient load action of the spring 16 then drives the elastic deformation of the fins 106 to allow the tail 62 of the rod 6 to pass. More specifically, the fins 106 move away from one another, or bend, to allow the tail 62 to pass, as shown by arrows F14 in FIG. 14. The bending F14 of the fins 106 is in practice done transversely to the axis X62. Thus, the rod 6 slides axially forward and the piston is moved inside the syringe body. Consequently, when the end-piece 10 leaves its forward position, i.e., moves toward its withdrawn position, the means blocking the forward movement of the rod 6 are deactivated and the injection begins, as symbolized by a drop G in FIG. 14. The forward movement of the rod 6 is shown in FIG. 14 by an arrow F15. In this embodiment, it is not necessary for the end-piece 10 to reach the withdrawn position to deactivate the means blocking the forward movement of the rod 6. In fact, these means are deactivated when the end-piece 10 leaves its forward position. Furthermore, the elastic finger 69 rubs against the surface S460 of the stop 46 during the movement of the rod 6.

If the user accidentally withdraws the injector 1 from his thigh during the injection, the end-piece 10 returns to its forward position under the resilient load action of the spring compressed during the withdrawal of the end-piece 10.

When the end-piece 10 reaches the forward position, the surfaces S108B of the ends 108 of the fins 106 abut against the surfaces S46 of the seats 46. The fins 106 return to their initial position in contact with the seats 46 and the seats 46 then once again prevent the elastic deformation of the fins 106. The tail 62 of the rod 6 is once again held a vise between the two fins 106, which prevents the forward movement of the rod 6. Thus, the return of the end-piece 10 to its forward position drives the reactivation of the means blocking the forward movement of the rod 6 and the injection is then temporarily stopped. In this embodiment, it is necessary for the end-piece 10 to come into the forward position to take advantage of the bearing of the seats 46 and thus to reactivate the means blocking the forward movement of FIG. 6.

To continue the injection, the user once again presses the injector 1 on his thigh and presses to cause the end-piece 10 to withdraw. As previously explained, the withdrawal of the end-piece 10 involves resuming the forward movement of the rod 6 and continuing the injection.

At the end of the injection, the finger 69 of the rod 6 is no longer blocked by the seat 46 and regains its initial shape by elastic return, as shown by arrow F16 in FIG. 15. The elastic return of the finger 69 [may] be interpreted as a pivoting movement, and the finger 69 becomes housed in a space E1 positioned between a front end for 462 of the seat 46 and the shoulder 109 of a fin 106. In FIG. 15, the end of the injection phase is symbolized by a drop G', the outline of which is shown in broken lines.

When the user withdraws the auto-injector 1 from his thigh, the end-piece 10 moves forward under the action of the resilient load from the spring and returns to the forward position. The finger 69 of the rod 6 is again slightly compressed in contact with the surface S109 of the fin 106, to allow the fins 106 to pass. In other words, the fins 106 force the passage toward the forward position by compressing the finger 69. Next, once the shoulder 109 has protruded past the finger 69, i.e., the shoulder 109 has arrived in front of the finger 69, the finger 69 regains its initial shape by elastic return and becomes housed against the shoulder 109 of the fin 106. Thus, the finger 69 hinders the withdrawal of the fins 106 from the end-piece 10. The finger 69 can therefore be interpreted as a means for blocking the end-piece 10 in a forward end of injection position. This means opposes the withdrawal of the end-piece 10 after the injection. Thus, the user does not risk injuring himself with the needle 84 by accidentally pressing on the end-piece 10, since the end-piece 10 is blocked in the forward position.

Alternatively, the automatic injector 1 can be used to perform an injection on any other part of the body other than the thigh.

Alternatively, the active ingredient P used may be a medicament other than adrenaline or an atropine solution.

In an alternative that is not shown, the automatic injector 1 can be refillable.

The technical features of the alternatives and embodiments considered above may be combined to create new embodiments of the invention.

What is claimed is:

1. An automatic injector, comprising:
    a cap ")", extending along a longitudinal axis,
    a syringe for injecting a medicament, which is positioned inside the cap and which includes a needle, a needle protector, a body and a piston,
    a rod for pushing the piston inside the body, said rod being moved axially forward by a resilient load force exerted by a first spring, during an injection,
    an end-piece for protecting the needle, which is movable axially around the needle and against a resilient load force exerted by a second spring, between a forward position where the end-piece surrounds the needle and a withdrawn position, where the needle is exposed,
    a block configured to block forward movement of the rod, wherein the block is configured to be deactivated when the end-piece is moved toward its withdrawn position or reaches that position, and to be reactivated during the injection when the end-piece is moved toward its forward position or arrives in that position, said block comprising:
    a first lever, which is provided to block a forward movement of a rack arranged on the rod, the end-piece comprising a cam freeing the blocking action of first lever on the rack, said cam driving a tilting of the first lever toward a free configuration of the rack when the end-piece arrives in the withdrawn position, or
    two elastic fins, which belong to the end-piece and which are positioned on either side of the push rod, and two stops blocking the elastic fins in a position where the elastic fins keep the rod in a vise between them.

2. The automatic injector according to claim 1, wherein the first lever is elastically deformable and is deformed at the beginning of the injection in contact with the cam, to tilt off a passage trajectory of the rack.

3. The automatic injector according to claim 2, wherein the first lever is configured to resume its initial shape by elastic return if the end-piece returns toward its forward position during the injection and wherein this elastic return causes a part of the first lever to be housed in an indentation of the rack, thus preventing the forward movement of the rod.

4. The automatic injector according to claim 1, wherein the elastic fins each comprise a bearing surface on a stop, which is inclined relative to a longitudinal axis of the rod parallel to the longitudinal axis and that is complementary to a contact surface of the stop.

5. The automatic injector according to claim 1 further comprising a lock configured to lock the end-piece in a forward end of injection position, which opposes the withdrawal of the end-piece after injection.

6. The automatic injector according to claim 5, wherein the lock comprises an elastic finger belonging to the rod, which pivots at the end of the injection by elastic return, to block a withdrawal of the elastic fins of the end-piece.

7. The automatic injector according to claim 5, wherein the lock comprises a second lever blocking the movement of the end-piece, which is provided to cooperate with a bolt worn by the end-piece, this second lever opposing the withdrawal of the bolt of the end-piece when the end-piece is in the forward end of injection position.

8. The automatic injector according to claim 7, wherein the second lever is elastically deformable and in that the rod comprises an anvil maintaining the second lever during the injection, which prevents the second lever from deforming in contact with the bolt as long as the injection is not complete.

9. The automatic injector according to claim 8, wherein the anvil is arranged on the rod to stop maintaining the second lever at the end of the injection, the second lever then deforming in contact with the bolt to free the movement of the end-piece toward its forward end of injection position and regaining its initial shape by elastic return in a position where the second lever opposes a withdrawal of the bolt of the end-piece.

* * * * *